(12) United States Patent
Walden et al.

(10) Patent No.: US 7,783,429 B2
(45) Date of Patent: Aug. 24, 2010

(54) PEPTIDE SEQUENCING FROM PEPTIDE FRAGMENTATION MASS SPECTRA

(75) Inventors: Peter Walden, Berlin (DE); Rodion Demine, Berlin (DE)

(73) Assignee: Charite'-Universitatsmedizin Berlin, Berlin (DE)

( * ) Notice: Subject to any disclaimer, the term of this patent is extended or adjusted under 35 U.S.C. 154(b) by 683 days.

(21) Appl. No.: 11/060,591

(22) Filed: Feb. 18, 2005

(65) Prior Publication Data

US 2006/0190183 A1   Aug. 24, 2006

(51) Int. Cl.
*G06F 19/00* (2006.01)
*G11C 17/00* (2006.01)
*H01J 49/26* (2006.01)

(52) U.S. Cl. .............................. 702/19; 702/27; 365/94; 250/282

(58) Field of Classification Search ........................ None
See application file for complete search history.

(56) References Cited

U.S. PATENT DOCUMENTS 6,582,965 B1 * 6/2003 Townsend et al. ............. 436/89

OTHER PUBLICATIONS

Taylor et al. Sequence Database Searches via de Novo Peptide Sequenceing by Tandem Mass Spectrometry. Rapid Communications in Mass Spectrometry vol. 11, pp. 1067-1075 (1997).*

* cited by examiner

*Primary Examiner*—John S Brusca
(74) *Attorney, Agent, or Firm*—Sughrue Mion, PLLC

(57) ABSTRACT

The invention relates to a method of peptide sequencing from peptide fragment mass data, wherein a plurality of candidate peptide sequences are determined comprises the steps of: calculating peptide fragment masses, searching a plurality of peak data for masses matching said calculated peptide fragment masses, annotating all permutations of said peak data with amino acid sequences that correspond to the calculated peptide fragment masses, extending said potential sequences to resulting masses with additional matching masses, extending stepwise additions until the resulting masses correspond to parental peptide masses or said parental peptide masses minus the mass of water, and identifying at least one peptide sequence by deleting sequences that can not be extended to endpoints of said parental peptide masses, and deleting identical sequences generated.

10 Claims, 8 Drawing Sheets

Fig. 4C

| Query | Score | Letters | Identities | Positives | BLAST Score | E |
|---|---|---|---|---|---|---|
| FQNALLVR | 3.87 | 8 | 8/8 | 8/8 | 28.60 | 1.20 |
| FQNAILVR | 3.87 | 8 | 7/8 | 7/8 | 25.20 | 12.00 |
| FAGNAILVR | 3.55 | 9 | 7/7 | 7/7 | 24.40 | 22.00 |
| FGANAILVR | 3.66 | 9 | 7/7 | 7/7 | 24.40 | 22.00 |
| FGANAILVR | 3.66 | 9 | 7/7 | 7/7 | 24.40 | 22.00 |
| FGANAILVR | 3.66 | 9 | 7/7 | 7/7 | 24.40 | 22.00 |
| FGANAILVR | 3.66 | 9 | 7/7 | 7/7 | 24.40 | 22.00 |
| FKNALLVR | 3.87 | 8 | 7/8 | 7/8 | 24.00 | 30.00 |

Query details

FQNALLVR    3.87    8    8/8    8/8    28.60    1.20

>gi|113576|sp|P02768|ALBU_HUMAN Serum albumin precursor
    Length = 609

Score = 28.6 bits (60), Expect = 1.2
Identities = 8/8 (100%), Positives = 8/8 (100%)

Query:  1    FQNALLVR  8
             FQNALLVR
Sbjct:  427  FQNALLVR  434

Fig. 4D

SEQUIT 2.0 - FQNALLVR.txt

Sequit | Blast | Digest |

Open    Clear                                    PMF tolerance 0.20    missed cleavages 1

Sequence info protein mass: 69,321.01
sequence coverage: 24%
matched masses: 14 from 32
PMF tolerance: 0.20
missed cleavages: 1

MKWVTFISLLFLFSSAYSRGVFRRDAHKSEVAHRFKDLGEENFKALVLIAFAQYLQQCPFEDH-
VKLVNEVTEFAKTCVADESAENCDKSLHTLFGDKLCTVATLRETYGEMADCCAKQEPERNECF-
LQHKDDNPNLPRLVRPEVDVMCTAFHDNEETFLKKYLYEIARRHPYFYAPELLFFAKRYKAAFT-
ECCQAADKAACLLPKLDELRDEGKASSAKQRLKCASLQKFGERAFKAWAVARLSQRFPKAEF-

Peptide fragments (with masses 500 - 3000)

| theoretical mass | measured mass | error | sequence |
|---|---|---|---|
| 890.50 | | | LKCASLQK |
| 892.43 | | | DEGKASSAK |
| 915.41 | | | CCKHPEAK |
| 927.48 | 927.49 | -0.01 | YLYEIAR |
| 940.44 | 940.43 | 0.01 | DDNPNLPR |
| 951.43 | | | DLGEENFK |
| 960.56 | 960.54 | 0.02 | FQMALLVR |
| 973.52 | | | SEVAHRFK |
| 984.48 | | | TYETTLEK |
| 1000.60 | | | QTALVELVK |
| 1002.56 | | | TPVSDRVTK |
| 1013.42 | | | ETCFAEEGK |

Unmatched masses

| mass |
|---|
| 983.50 |
| 1093.43 |
| 1213.55 |
| 1331.87 |
| 1430.66 |
| 1452.64 |
| 1483.72 |
| 1489.63 |
| 1583.16 |

Exit

PEPTIDE SEQUENCING FROM PEPTIDE FRAGMENTATION MASS SPECTRA

The invention relates to techniques for peptide sequencing from peptide fragmentation mass spectra.

BACKGROUND OF THE INVENTION

The progress in the genome projects rapidly advances the development of new strategies in functional genomics that aim at elucidating the biological function of the genes by global analyses of protein expression and modification. Proteomics is a key technology in this context which allows the analysis of thousands of proteins in a single 1- or 2-dimensional gel electrophoresis. However, the identification of these proteins is still time-consuming and the rate-limiting step slowing the progress in functional genomics.

Mass spectrometry is capable of rapid, accurate and sensitive analysis of biomolecules and is increasingly used to obtain structural information on proteins and peptides. As yet, the identification of proteins by mass spectrometry is done mostly by protein fragment fingerprinting which involves enzymatic fragmentation of the protein, determination of the masses of the resulting fragments and comparison of their patterns with theoretical fragmentation patterns calculated from database sequences. With the increasing complexity of the sequence databases, however, there is a growing need for sequence information from the proteins. Accurate sequence information will translate into more accurate and faster database searches and is prerequisite for the detection of mutations and the identification of homologues of known proteins from species with yet not-sequenced genomes. In addition, the identification of biologically active peptides such as MHC-bound T cell epitopes, some peptide hormones and peptide antibiotics requires complete de novo sequencing, i.e. deduction of the peptide sequences directly from the mass spectra.

MALDI-TOF mass spectrometry is widely preferred for the detection of peptide masses because MALDI generates monocharged ions. ESI-MS/MS techniques, on the other hand, are favoured for the sequence determination. ESI-MS/MS spectra can be interpreted by several sequencing strategies including database searches with MS/MS data or peptide sequence tags, and new programs for de novo sequencing. The combination of these two MS technologies is currently seen as the best approach to proteome analyses. However, this combination comes with severe disadvantages as it requires two expensive instruments, is, despite attempts towards automation, time-consuming and labor-intensive and requires to split the often precious samples for preparation for the two different ionization techniques which increases the labor involved and reduces the sensitivity of the analyses.

In principle, the sequence of a peptide can be deduced from the MALDI-TOF post-source decay (MALDI-PSD) or collision-induced dissociation (MALDI-CID) fragmentation spectra. However, experimental spectra are very complex, often incomplete in that not all possible fragments are produced and marred by erroneous signals which can not be assigned to a known mode of peptide fragmentation. The mass accuracy of MALDI-PSD or -CID measurements is relatively low. The currently most extensively applied approaches for extracting peptide sequences from mass spectra compare the fragment masses to theoretical fragment masses calculated from database sequences (Perkins et al. *Electrophoresis.* 1999; 20: 3551; Creasy et al. *Proteomics.* 2002; 2: 1426; Field et al. *Proteomics.* 2002; 2: 36). The success of these approaches depends on the presence of the corresponding sequence in the databases. New, yet unknown or modified or mutated proteins or peptides can not or only exceptionally be identified.

Disintegration of peptides in the MALDI-TOF mass spectrometer produces daughter ions of different categories, as shown in FIG. 1 (Chaurand et al. *J Am Soc Mass Spectrom.* 1999; 10: 91). With both, laser-induced dissociation and collision-induced dissociation peptide desintegrate preferentially at main chain bonds. The resulting fragments that contain the C-terminus of the original peptide are called y-series fragments, those with the N-terminus b-series fragments. Both types of fragments may undergo further decompositions to yield additional fragment series. These fragment series extend to different positions in the sequence, ideally, to cover the entire sequence. The mass difference between two adjacent fragments of a series corresponds to the mass of the amino acid in the corresponding sequence position. In addition to the terminal fragments, internal fragments lacking both terminal amino acids as well as immonium ions corresponding to single amino acids are produced. The loss of ammonia is observed for all classes of ions with the exception of the immonium ions. Internal fragments occasionally lose carbonic monoxide. Additional loss of water is observed for fragments containing serine or threonine, and also other amino acids can cause specific secondary fragmentations. Positively charged amino acids at the C-terminus as in tryptic fragments of proteins enhance the y series and facilitate their identification. Positively charged amino acids at or near the N terminus lead to loss of carbonic monoxide in the b but not in the y fragments. Side chain fragmentations are rare but observed in different amino acids including argenine and the aliphatic isobars leucine and isoleucine.

Several strategies were proposed for enhancing the daughter ion series containing one of the terminal amino acids thus to facilitate sequence determination. Among these strategies are comparative analyses based on the exchange of hydrogen and oxygen isotopes at or selective chemical derivatization of the terminal amino acid (Heller et al. *J Am Soc Mass Spectrom.* 2003; 14: 704; Mo et al. *Rapid Commun Mass Spectrom.* 1997; 11: 1829; Uttenweiler-Joseph et al. *Proteomics.* 2001; 1: 668). While these strategies help in special cases they have not been adapted widely because in most cases they are laborious, can produce even more complex spectra and lead to loss of sample material and thereby to reduced sensitivity.

SUMMARY OF THE INVENTION

The disclosed teachings are aimed at solving some of the above-discussed problems in the related art. It is an object of the invention to provide improved techniques for peptide sequencing from peptide fragmentation mass spectra which provides more reliable and database independent sequencing results.

According to an aspect of the invention a method of peptide sequencing from peptide fragment mass data is provided, said method comprising the steps of providing peptide fragment mass data, said fragment mass data comprising a plurality of peak data, deriving a plurality of candidate peptide sequences from said peptide fragment mass data, calculating mass spectra for each candidate peptide sequence from said plurality of candidate peptide sequences, and comparing said calculated mass spectra to said peptide fragment mass data for providing at least one identified peptide sequence.

In a specific enhancement the step of deriving said plurality of candidate peptide sequences comprises the following steps: calculating peptide fragment masses by adding to masses of a proton, hydronium ion, b1 ion or y1 ion masses of one amino acid or more amino acids, searching said plurality of peak data for masses matching said calculated peptide fragment masses, annotation to potential sequence an amino acid or amino acids in all permutations that correspond to said calculated peptide fragment masses for which matches were found in said plurality of peak data, extending resulting sequences from matching masses by adding stepwise masses of one amino acid or more amino acids and searching for masses in said plurality of peak data that match resulting masses, extending said stepwise additions until said resulting masses correspond to parental peptide masses or said parental peptide masses minus the mass of water, depending on whether b or y ion series sequences are calculated, dismissing sequences that can not be extended to endpoints of said parental peptide masses, and reducing identical sequences generated by computing said b and said y ion series and by using combinations of amino acids to one sequence.

Compared to prior art methods of peptide sequencing, it is an advantage of the invention that peptide sequences are derived directly from the experimental fragment mass data. Preferentially complete information from the experimental fragment mass data is examined in the procedure for peptide sequencing.

Another aspect of the invention is a computer program product that includes a computer readable media including instructions to enable a computer to perform the techniques disclosed herein.

BRIEF DESCRIPTION OF THE DRAWINGS

The above aspect and other advantages of the disclosed teachings will be more apparent by describing an embodiment in greater detail with reference to the accompanying drawings, in which:

FIG. 4C the output window for the identification of PROTEIN 1; and

FIG. 4D the output window for the identification of PROTEIN 1 as well as listing (Unmatched masses) of fragments identified in the PMF which can not be assigned unambiguously to PROTEIN 1.

DETAILED DESCRIPTION OF THE EMBODIMENTS

Measurements were done with Bruker-Daltonics reflector MALDI-TOF mass spectrometer Reflex II with PSD and CID capabilities. Argon was used as a collision gas, α-HCCA as matrix. The samples were prepared by the dried droplet procedure. A peptide mix containing angiotensine I, angiotensine II, and substance P was used for external mass calibration. The PSD and CID measurements were calibrated with ACTH clip. Mass accuracy of peptide mass measurement was 0.1 Da. Mass accuracy of peptide fragment mass measurement was 0.7 Da. The synthetic peptides were custom-synthesized by EMC-microcollections, Tübingen, Germany. 10-100 pmol of peptide sample was used for the analyses. Tryptic peptides were generated by digest of albumin from a 1-dimensional SDS PAGE electrophoresis gel band. The database search was done with BLAST (BLASTP 2.2.5) using SwissProt of October, 2003. MASCOT MS/MS ion searches were performed without taxonomy restrictions using NCBI database as of October, 2003.

Figure 1:
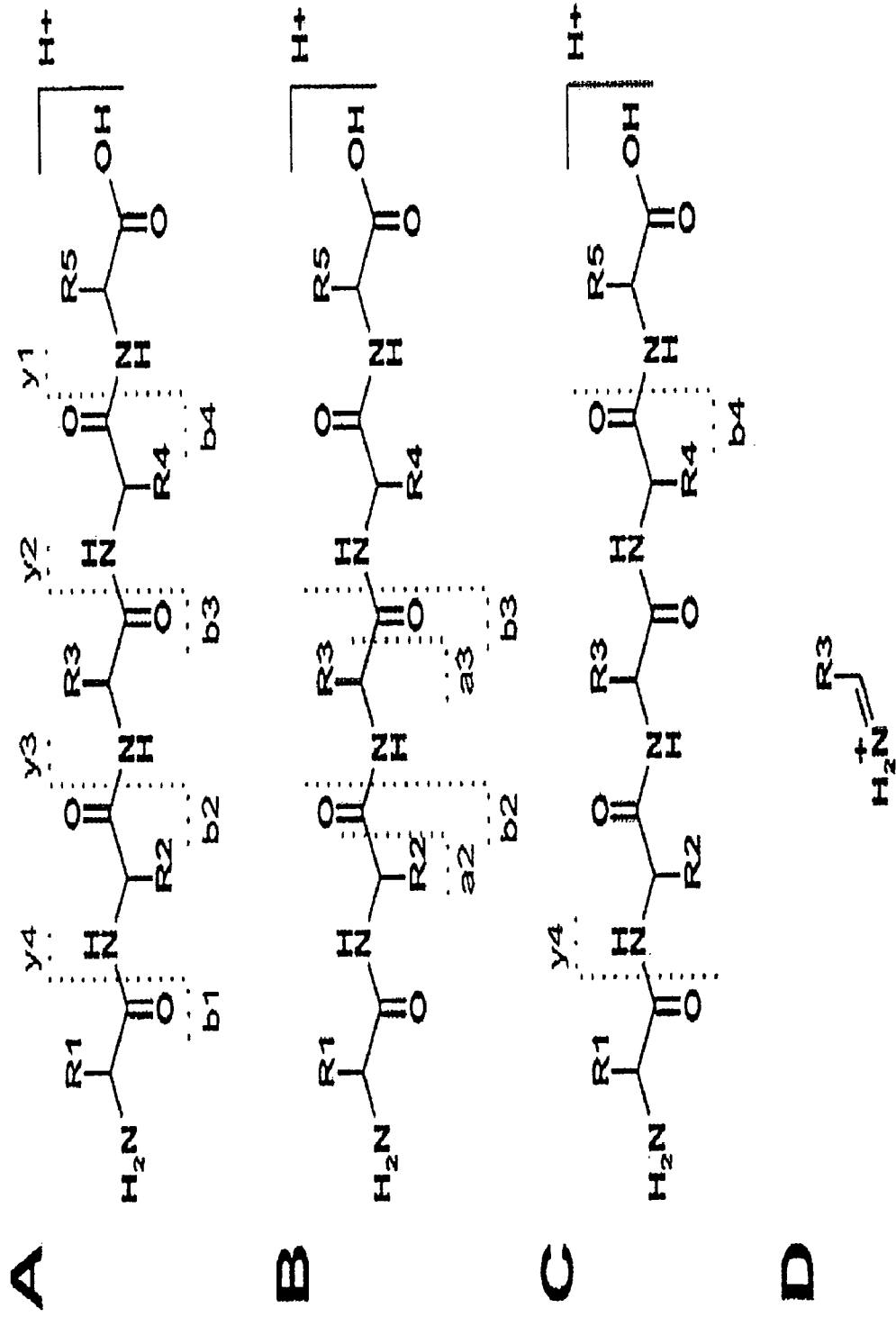
FIG. 1 main chain fragmentation patterns for peptide sequencing by mass spectrometry.
Figure 2:
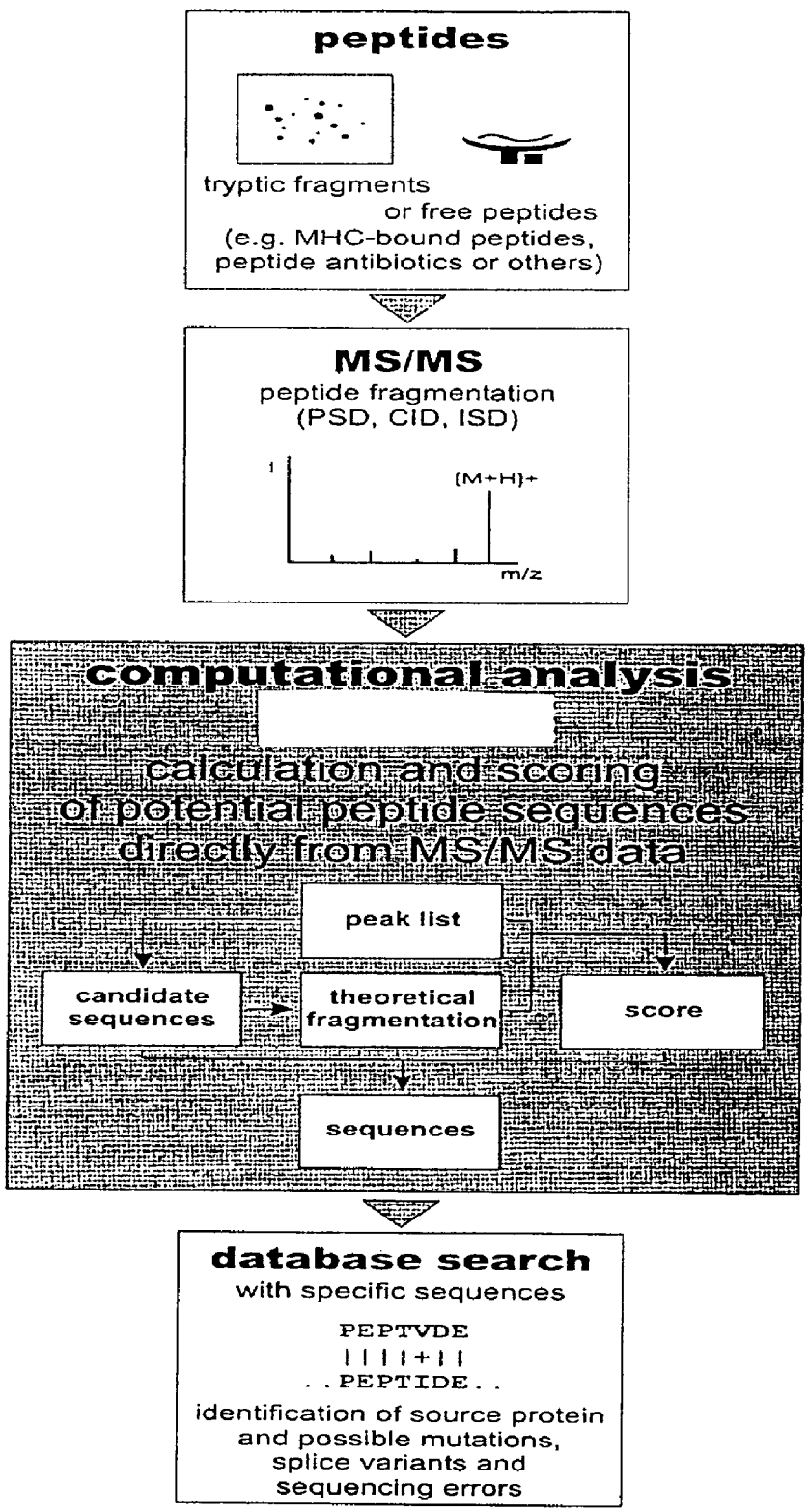
FIG. 2 a flow chart depicting a de novo peptide sequencing method.

Peptide sequences from MALDI-PSD or CID peak lists and the masses of the parental peptide ions were computed by the following procedures. FIG. 2 shows a flow chart depicting the de novo peptide sequencing method used. Peak lists obtained from tandem mass spectrometry of peptides fragmented by MALDI-TOF collision-induced dissociation or post-source decay were utilized. The input data files are computed to derive the sequences of the peptides independent from database sequences and scored according to the degree to which the experimental fragment masses match the fragment mass profile calculated from the proposed peptide sequence. The peptide sequences determined may then be compared to database sequences for validation and/or to identify the source proteins from which the peptides were derived.

Following a preferred embodiment of the sequencing method is described in further detail.

The computation of a sequence form a fragmentation mass spectrum (e.g. MALDI-PSD, CID) is initiated with the mass of a proton or of a b1 ion.

The masses of single amino acids or of combinations of 2 or more amino acid masses are added. The number of amino acids to be combined is pre-set.

The resulting masses are compared to the peak list of the mass spectrum. In the case a match is found within the fragment tolerance, the corresponding amino acid or amino acids in all permutations are annotated as potential amino acid sequence.

The resulting mass is used as starting point for the next cycle of addition of the masses of amino acids and of amino acid combinations with subsequent searches for matching masses in the peak list of the spectrum. These cycles are repeated until the computed peptide mass matches the largest b ion mass series in the peak list. The largest b ion mass series is the parental peptide ion mass minus the mass of an $H_2O$ molecule.

Sequences that can not be extended to this largest b ion mass series are deleted.

The same sequence computation is done for the y ion series. Here the computation is initiated with the mass of the hydronium ion or of the y1 ion. The calculation of the sequence is complete when a match to the parental peptide ion mass is found. The sequence resulting from the computation of the y ion series is the reverse of the sequence resulting from the computation of the b ion series. Of course it is irrelevant whether the computation is initiated with hydronium ion or y1 ion or whether it is initiated with a proton or a b1 ion.

Sequences that can not be extended to parental peptide ion mass are deleted.

Identical sequences, which might be deducted from the different ion series or from the same ion series by using different amino acid combinations are, deleted.

The parental ion mass can be determined with much higher accuracy than the fragment masses. Therefore, the mass tolerances for the parental ion and for the MS/MS fragments are determined independently. The combinations of amino acids used in the computation of the sequences bridge gaps in incomplete b or y ion series and correct false positive annotations of sequence amino acids due to errant masses in the peak list. Furthermore, in cases of incomplete spectra, i.e.

missing daughter ion masses, or of additional, unaccountable masses, several permitted sequences may be produced.

The calculated sequences are scored according to the degree to which they fit the experimental mass spectra. For scoring, theoretical spectra are calculated for the proposed peptide sequences according to the known fragmentation rules. The proposed sequences are graded by the degree to which their theoretical fragmentation profiles match the experimental peak lists. The scores are calculated as the numbers of experimental fragments matching the theoretical fragments, normalized by the numbers of amino acids in the sequence. In cases of different output sequences due to incomplete input spectra, database searches for matching sequences are performed.

With the method described, the calculations of peptide sequences from mass spectra are controlled and validated at three check points, two internal and one external. The first check point is that the stepwise computations of the sequences must result in the parental peptide mass. The second check point is the scoring of the computed sequences by comparing the theoretical fragmentation masses generated from the sequences with the experimental spectra. The third check point, which is optional, is the comparison of the computed peptide sequence with the sequences in databases.

The invention makes use of one or more databases herein a database may be for example, a flat-file database, or a relational database or an XML database. Commonly used databases for the foregoing invention are those which contain information on protein or peptide sequences. Examples are SWISS-PROT, BIND, INTERPRO, GENBANK, NCBI, and EMBL. The databases may present within the system that runs the method according to the invention or located externally.

To test the above procedure twenty three peptides were chosen that represented a range of different amino acid compositions and sequences, fifteen are listed in sequence databases, six variants of database sequences and two completely artificial. These peptides were subjected to MALDI-PSD analyses, one peptide also to CID. The results of the test are depicted in Table 1.

In Table 1, the peptides indicated in the column 'Peptide' were subjected to MALDI-PSD or, in one case, MALDI-CID fragmentation analyses. Peptide sequences in bold-face letters denote peptides which are not listed in any sequence database. [M+H]+ is the mass of the parent peptide ion. The results of the fragmentation analyses are given as numbers of b and y fragments, and immonium ions (i) identified. The outcomes of the analyses are given as scores which are the degree to which experimental and theoretical fragment mass profiles match normalized by the numbers of amino acids in the sequence. 'Match' lists the number of experimentally determined masses which are accounted for by the mass profiles calculated from the proposed sequences. 'Cov' is the coverage of the experimental results by the theoretical spectra. 'Sequence' gives the peptides sequences determined by Sequit with the correct sequence highlighted with bold-face letters. L is set to indicate the isobaric amino acids leucine and isoleucine in the result sequences. For comparison, standard MASCOT analyses were done for all the peptides whose sequences are listed in the sequence databases implemented in MASCOT. The results of these analyses are given according to the MASCOT grading as a significant homology (s.h.) or as a random match. Significant homology indicates that the experimental data represents the identified or very similar sequence. Random match is irrelevant. n.f. stands for not found, n.t. for not tested. The calculations shown in this table were performed with maximally two combined amino acids.

TABLE 1

| Peptide | [M + H]+ | Ions | | | | Sequit | | | | Mascot |
| | | n | b | y | i | Score | Match | Cov.[%] | Sequence | Match |
| --- | --- | --- | --- | --- | --- | --- | --- | --- | --- | --- |
| PSD sequencing | | | | | | | | | | |
| DRVYIHPF | 1046.8 | 8 | 4 | 7 | 5 | 5.25 | 42 | 53 | DRVYLHPF | random |
| ILAKFLHWL | 1140.74 | 9 | 7 | 6 | 2 | 4.33 | 39 | 68 | PTVKFLHWL | |
| | | | | | | 4.33 | 39 | 68 | TPVKFLHWL | |
| | | | | | | 4.33 | 39 | 68 | VVVKFLHWL | |
| | | | | | | 4.22 | 38 | 67 | LLAKFLHWL | s.h. |
| IMDQVPFSV | 1035.53 | 9 | 8 | 7 | 1 | 3.77 | 34 | 72 | LNFLVPFSV | |
| | | | | | | 3.66 | 33 | 70 | LMDQVPFSV | — |
| | | | | | | 3.66 | 33 | 70 | LMDKVLMSV | |
| | | | | | | 3.66 | 33 | 70 | LDMKVPFSV | |
| | | | | | | 3.66 | 33 | 70 | LNFLVLMSV | |
| | | | | | | 3.66 | 33 | 70 | LNMEVPFSV | |
| ITDQVPFSV | 1005.54 | 9 | 5 | 4 | 2 | 3.33 | 30 | 61 | EPCKVMLVS | |
| | | | | | | | | | ... | |
| | | | | | | 3.11 | 28 | 57 | LTDQVPFSV | n.f. |
| KTWGQYWQV | 1195.67 | 9 | 8 | 7 | 2 | 4.77 | 43 | 72 | KTWGQYWQV | random |
| PVKTYDLKL | 1076.7 | 9 | 8 | 6 | 2 | 4.44 | 40 | 70 | PVKTYDLKL | — |
| | | | | | | 4.44 | 40 | 70 | PARTYDLKL | |
| PVKTKDLKL | 1041.67 | 9 | 8 | 6 | 2 | 4.66 | 42 | 52 | PVKTKDLKL | — |
| RGYVYQG | 842.5 | 7 | 6 | 3 | 2 | 4.00 | 28 | 58 | RGYVYQG | random |
| RPPGFSPFR | 1060.5 | 9 | 8 | 9 | 3 | 6.55 | 59 | 44 | RPPGFSPFR | random |
| SAYGEPRKL | 1020.6 | 9 | 6 | 5 | 5 | 3.77 | 34 | 59 | SAYGEPRKL | n.f. |
| | | | | | | 3.77 | 34 | 59 | SYAGEPRKL | |
| VLYRYGSFSV | 1190.64 | 10 | 6 | 7 | 4 | 5.55 | 50 | 60 | VLYRYGSFW | |
| | | | | | | | | | ... | |
| | | | | | | 5.10 | 51 | 61 | VLYRYGSFSV | random |
| YLEPGPVTA | 946.42 | 9 | 8 | 8 | 4 | 5.00 | 45 | 54 | YLEPGPVTA | s.h. |
| YMNGTMSQV | 1030.3 | 9 | 6 | 6 | 1 | 3.55 | 32 | 63 | MYNGTMSKV | |
| | | | | | | | | | ... | |
| | | | | | | 3.33 | 30 | 59 | YMNGTMSQV | random |

TABLE 1-continued

|  |  | Ions |  |  |  | Sequit |  |  |  | Mascot |
| --- | --- | --- | --- | --- | --- | --- | --- | --- | --- | --- |
| Peptide | [M + H]+ | n | b | y | i | Score | Match | Cov.[%] | Sequence | Match |
| PSD sequencing of peptides with similar amino acid composition | | | | | | | | | | |
| FLWGPRALV | 1058.54 | 9 | 5 | 4 | 4 | 4.22 | 38 | 63 | FLWGPRALV | random |
| FLSVGPRALV | 1058.62 | 10 | 5 | 6 | 4 | | | | not calculated | — |
| RGYVYQGL | 955.5 | 8 | 6 | 1 | 2 | 3.62 | 29 | 49 | RYGVYANL | |
| | | | | | | | | | . . . | |
| | | | | | 3.50 | 28 | 47 | RGYVYQGL | random |
| RGYVYQLG | 955.49 | 8 | 8 | 2 | 4 | 4.62 | 37 | 61 | RGYVYQLG | — |
| GRYVYQGL | 955.42 | 8 | 6 | 5 | 3 | 5.00 | 40 | 69 | VNYVYKGL | |
| | | | | | | | | | . . . | |
| | | | | | 4.75 | 38 | 66 | GRYVYQGL | — |
| SIINFEKL | 963.55 | 8 | 7 | 5 | 4 | 4.87 | 39 | 49 | LSLNFEKL | |
| | | | | | 4.75 | 38 | 48 | SLLNFEKL | random |
| IISNFEKL | 963.48 | 8 | 6 | 5 | 1 | 3.87 | 31 | 60 | LLSNFEQL | |
| | | | | | 3.75 | 30 | 58 | LLSNFEKL | — |
| IISGGFEKL | 963.5 | 9 | 8 | 7 | 4 | 4.77 | 43 | 75 | LLSGGFEKL | — |
| PSD sequencing of peptides generated by the trypsin digestion of albumine isolated by SDS-PAGE | | | | | | | | | | |
| FQNALLVR | 960.6 | 8 | 5 | 5 | 1 | 3.87 | 31 | 78 | FQNALLVR | random |
| YLYEIAR | 927.52 | 7 | 3 | 6 | 2 | 2.85 | 20 | 83 | YLYELAR | random |
| | | | | | | 2.85 | 20 | 83 | LYYELAR | |
| | | | | | | 2.85 | 20 | 83 | EFYELAR | |
| | | | | | | 2.85 | 20 | 83 | FEYELAR | |
| CID sequencing | | | | | | | | | | |
| DRVYIHPF | 1046.57 | 8 | 6 | 5 | 5 | 4.12 | 33 | 58 | DRVYIHPF | n.t. |
| | | | | | | 4.12 | 33 | 58 | DRVYIHMI | |

Twenty-two of the twenty-three peptides were sequenced correctly (cf. Table 1). In thirteen cases the correct sequence was scored best among the proposed sequences, in ten of these as the only best scored sequence. In four cases the correct sequence was among the second-best scored and in four cases among the best three, one sequence was seventh rated. Only in one case no qualified sequence was obtained. For the angiotensin peptide DRVYIHPF which was analyzed by PSD as well as CID, both input data sets led to the correct sequences, however, the CID in contrast to the PSD spectrum allowed to identify isoleucine vs. leucine at position 5 by the detection of the 591.51 Da $d_a$ fragment produced by the isoleucine-specific side chain fragmentation. Only peptide FLSVGPRALV was not sequenced correctly with the set limit to two combined amino acid masses. Instead the sequence FLSVGPKVLV was proposed with a high score. However, the correct sequence was found when the number of combined amino acid masses was raised to three.

Alternative de novo sequencing strategies depend on complete series of b or y fragments. Of the data sets analyzed here only for the peptides RPPGFSPFR and RGYVYQLG a complete y- or b-fragment series were determined (Table 1, FIG. 3A). For all the other peptides successful sequence determination was based on incomplete sequences with an average coverage of all the experimental data by the theoretical peptide fragments of 65% (range 47 to 83%). Secondary mass spectra with complete y- or b-ion fragment series are rarely obtained which renders the alternative approaches to de novo sequencing very inefficient.

Figure 3A:
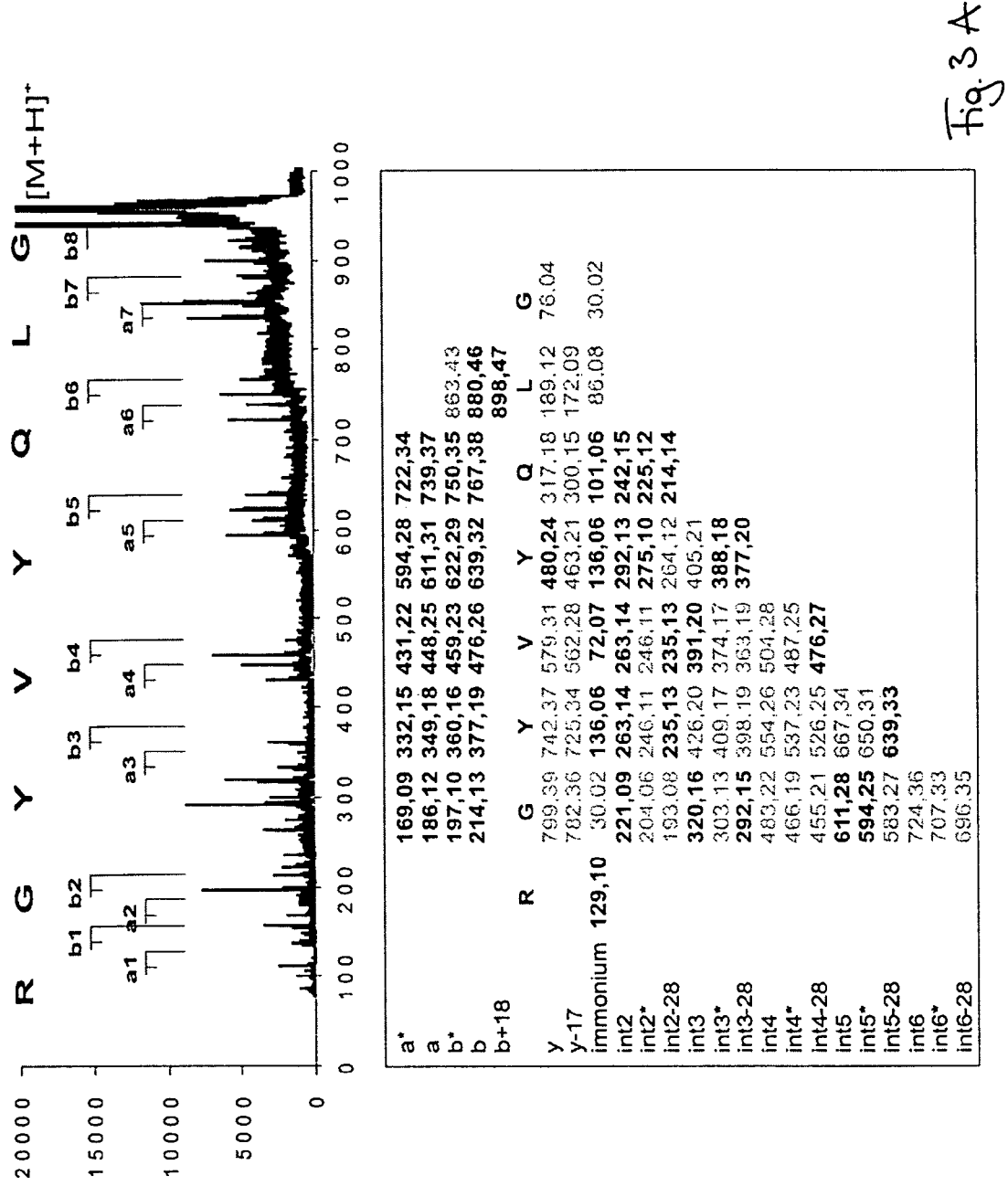
FIGS. 3A and 3B MALDI-PSD spectra and fragment masses calculated for the peptides RGYVYQLG and FLWG-PRALV, respectively.
Figure 3B:
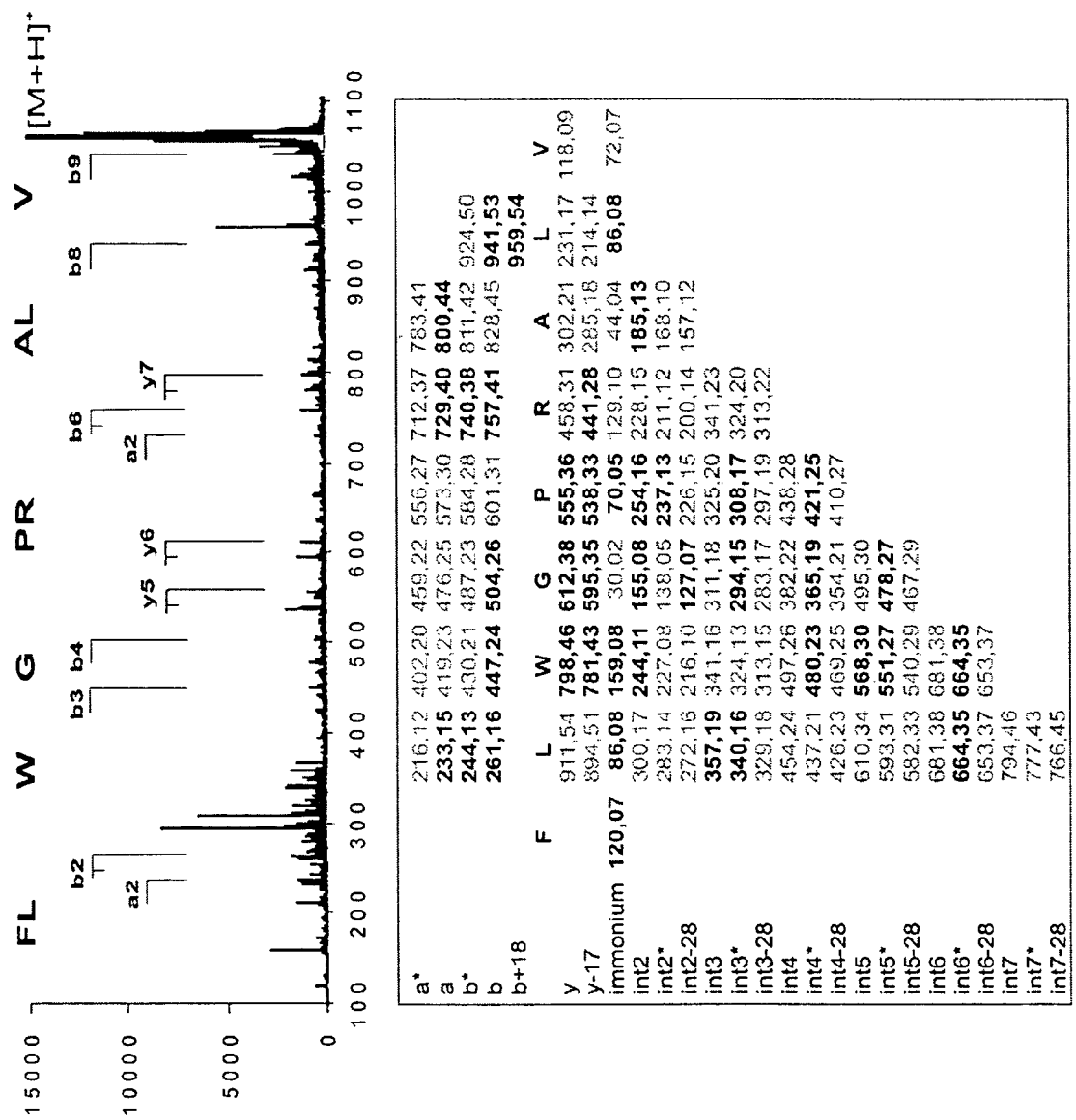

FIGS. 3A and 3B MALDI-PSD spectra and fragment masses calculated for the peptides RGYVYQLG and FLWG-PRALV, respectively. The peptides were analyzed by MALDI-PSD and the resulting fragment mass spectra evaluated with the peptide sequencing method described above. The experimentally determined fragment masses are compared with the fragment mass profile calculated from the sequence of the peptide determined with the procedure described above. The two examples were chosen to represent one case with a well-resolved terminal fragment series spectrum (FIG. 3A) and, on the other hand, a spectrum which is largely incomplete with respect to the terminal fragment series daughter masses essential for other de novo sequencing strategies (FIG. 3B) but which was interpreted correctly by the peptide sequencing method disclosed herein. The internal fragments are indicated with "int". int*, b* or a* indicate fragments that result from the dissociation of ammonium (int-17, b-17 or a-17). In the cases of fragments containing serine or threonine, water may dissociate off resulting in int-18, b-18 or a-18 secondary fragments.

The peptide FLWGPRALV is one of the extreme examples where 5 of 9 b- and 3 of 9 y-series fragments were detected and sufficed for sequence determination (Table 1, FIG. 3B). The b1, b5, b7 and b9 ions were missing and the C-terminal ion series contained only the y5, y6 and y7 fragment masses. Just 38 of 60 measured fragment masses could be explained by theoretical fragmentation. 44 of 103 mass differences corresponded to the amino acids C, D, E, H, K, M, N, Q, S, T and Y which are not part of the sequence. In such cases the probability of false positive sequences is high. Theoretical spectra of more than 200,000 peptide sequences that would match the spectrum to varying degrees were computed, however, the correct sequence was calculated to have the highest score which allowed an unequivocal sequence assignment (Table 1). Earlier attempts towards de novo peptide sequencing depend on the information provided by immonium ions and dipeptide masses (Chaurand et al. *J Am Soc Mass Spectrom.* 1999; 10: 91). The sequencing method described above was tested on spectra lacking such information. The PSD data acquisition for Wilms' tumour protein-derived GQQGSLGEQ peptide was interrupted to obtain a spectrum which lacks fragment masses below 280 Da. 100 candidate sequences matching the input data to different degrees were calculated with the correct sequence scored seventh. A batch BLAST search with all candidate sequences identified the correct sequence as the only 100% identity match with the sequence database entry of the correct sequence (Data not shown). No results were obtained with alternative approaches such as MASCOT.

The sequences of variant peptides as they may arise from mutations or peptides without corresponding entry in the sequence databases can not be determined by sequencing approaches that compare experimental spectra with theoretical spectra computed from the database sequences. Such variant and not-listed peptides were sequenced with equal success as natural peptide sequences listed in the databases. IMDQVPFSV is a peptide derived by a single amino acid exchange of methionine for threonine at position 2. Its sequence was calculated as second best match from the PSD spectrum. A database search identified ITDQVPFSV the natural counterpart of this peptide.

With its high-throughput capacities MALDI-TOF MS has evolved as an important tool for protein identification in proteomics. However, with increasing numbers of database entries the identification of proteins by tryptic fragment pattern analysis becomes increasingly unreliable which makes it necessary to obtain partial sequence information for proper protein assignment. The sequencing procedure described here can be incorporated in high-throughput data processing strategies and thereby become instrumental in routine proteome analysis. Trypsin creates fragments with positively charged amino acids at the C-terminus. Usually C-terminal positively charged amino acids produce relatively prominent y-series fragmentation spectra making their identification and overall sequence determination comparatively easy. However, with low amounts of peptides as they often are obtained from 2-dimensional electrophoresis gels in cases of low-abundant proteins, the PSD spectra of the tryptic fragments are usually incomplete. Sequencing of YLYEIAR generated by tryptic digestion of bovine serum albumin isolated by SDS polyacryl amide gel electrophoresis (SDS-PAGE) was possible from the y-series signals. Argenine at the C-terminus caused y and y-17 series signals of high intensity. The sequencing procedure described above proposed several equally rated candidate sequences including the correct sequence which all shared the same C-terminal sequence tag YELAR. This tag together with the tryptic fragment profile sufficed to identify the corresponding protein unequivocally. Sequencing of FQNALLVR was equally successful. The C-terminal amino acid was identified as arginine because of the presence of the 175 Da y1 ion. However, in cases where the y1 ion are missing from the PSD spectra of tryptic fragments, the C-terminal amino acid can be set to lysine or arginine to facilitate sequence determination.

Positively charged amino acids at or near the N-terminus facilitate the interpretation of the mass spectra by enhancing the b- and a-series fragments. Argenine at the N-terminus in RGYVYQGL peptide cause series of b, b-17, a, a-17 signals which can be easily identified. The peptide was sequenced as correctly as its variant RGYVYQLG where the two C-terminal amino acids were swapped (FIG. 3B). Similarly well-discriminating sequencing results were obtained for different variants of the peptides RGYVYQGL and SIINFEKL as well as for the artificially designed peptides PVKTYDLKL and PVKTKDLKL (Table 1).

The data used for the present study were obtained by MALDI-PSD and -CID analyses which are often discussed as unreliable. Despite this common belief, peptides were sequenced with a high success rate and accuracy. The described procedure of de novo peptide sequencing with possible subsequent similarity searches in databases has several advantages over alternative strategies such as MASCOT which is widely used in mass spectrometry-based protein and peptide analytics and proteomics.

First, the sequences are derived independent from databases directly from the mass spectra. Second, all the information in the spectra are considered and valued including the terminal fragments, internal fragments, immonium ions and parental ion masses. Third, the computation is controlled for consistency at two levels: The possibility to extend the subsequent rounds of sequence deduction to the final endpoint ions of the b and y series, and the degree to which theoretical spectra calculated from the proposed sequences match the experimental spectra. Fourth, subsequent database searches can be done with defined sequences which enhances the versatility of proteome analysis and allows for more accurate and faster database searches. Since MASCOT, like comparable strategies, ignores the frequently occurring internal fragments and identifies proteins or determines peptide sequences by comparing the experimental spectra with the immonium, a, b and y ions calculated for all database sequences, the chances for random matches and false-positive results increase with the growing numbers of database entries. Fifth, since the described method derives the sequences from the mass spectra independent of databases and the database searches are done with defined sequences, mutations can be identified. Sixth and for the same reasons, proteins and peptides not listed in databases can be analyzed. Seventh, in cases of incomplete input data sequence tags can be derived and used for database searches.

As is evident from the comparison of the results obtained with the sequencing procedure described herein and with MASCOT listed in Table 1, the sequencing procedure described here produces more accurate results than MASCOT. Of the 15 sequences of our test set which are listed in the NCBI sequence database only two were identified as significant match by MASCOT. In 11 cases the match was not significant meaning that the correct sequence was in the results lists but classified as random match and, therefore, discarded. In two cases the correct peptide was not listed at all. None of the variant peptides and none of the peptides missing from the databases could be identified with MASCOT.

In contrast, with the alternative method described herein all these sequences were determined correctly. The higher success rate of peptide sequencing with the sequencing procedure described here is likely correlated with the more extensive utilization of the information of the input mass spectra, the internal controls for the computation and the exclusion of potential biases introduced with the dependency on database sequences. Moreover, in cases of random matches, MASCOT selects peptides of varying amino acid composition whose theoretical fragmentation patterns match to the experimental data to the varying degree. The consequence is that the identification of the correct sequence is not possible. In contrast, the method described above utilizes all available information from incomplete input mass spectra to deduces sequence tags which then can be used for database searches.

Figure 4A:
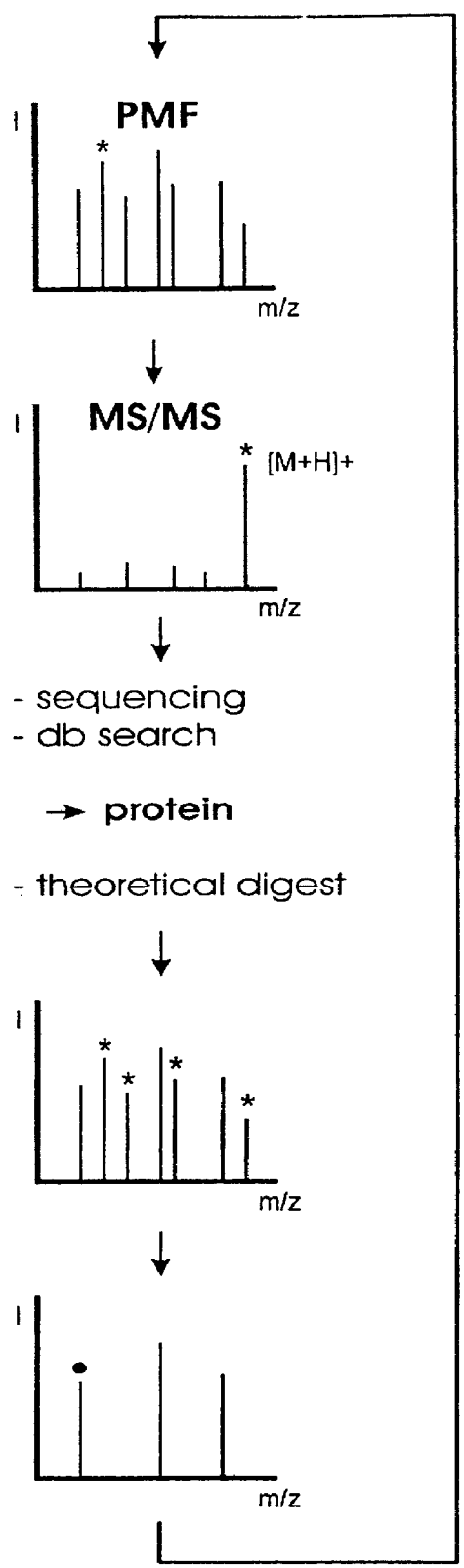
FIG. 4A a further embodiment of the invention, where the analysis of peptide data is combined with peptide mass fingerprinting (PMF)
Figure 4B:
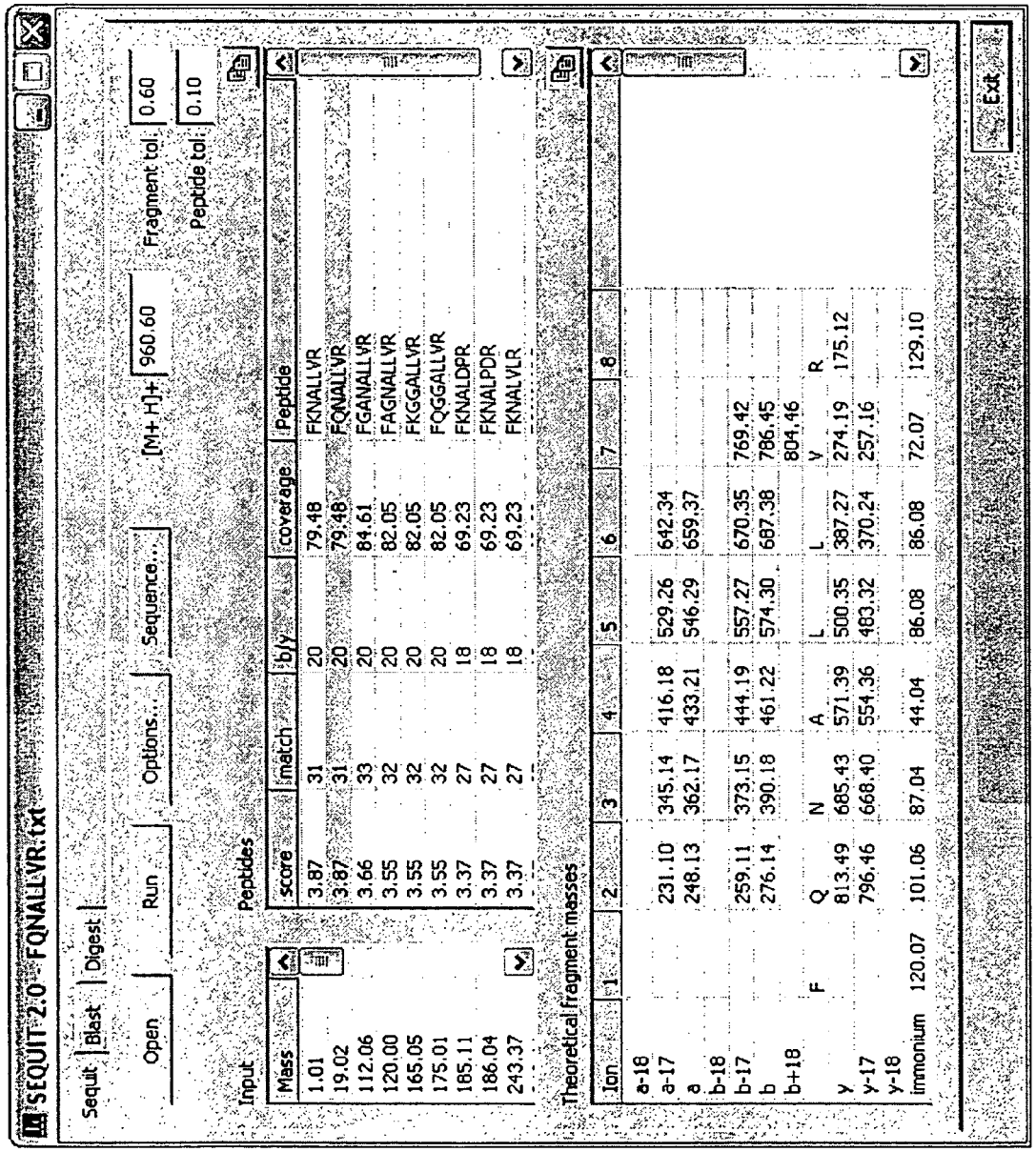
FIG. 4B the output window for peptide sequences as generated in step four of the general scheme shown in FIG. 4A.

As it is the case for other approaches, the success of de novo peptide sequence determination with the method described above depends on the quality of the input mass spectra. The more complete the spectrum the more reliable the proposed sequences will be. However, even with relatively incomplete spectra or spectra marred by erroneous signals, sequences could be deduced and used for defined database searches. The accuracy of sequence determination will increase with the accuracy of the mass spectrometry measurements. In addition to MALDI-TOF-PSD, the method was successfully tested with tandem mass spectra produced by MALDI-TOF/TOF, ESI-QTOF and ESI-Quad mass spectrometers. The advantages of the method described above will, thus, manifest itself especially with the new MALDI-TOF/TOF mass spectrometry technology with its high- FIG. 4A schematically shows a further embodiment of the invention. Here, the analysis of peptide data is combined with peptide mass fingerprinting (PMF). In a first step, (i) PMF is performed on a protein or a protein mixture. Such proteins may stem from e.g. column purification or 1D or 2D gel electrophoresis. The protein is ideally digested or otherwise fragmented before it undergoes PMF. On form of fragmentation is a trypsin digest. The PMF analysis results in a mass spectrum representing all fragments of the protein or the protein mixture generated by fragmentation. In a second step, (ii) a first peptide (representing a fragment of PROTEIN 1) is isolated e.g. by the ion gate method. In a third step, (iii) the isolated peptide is analyzed, by tandem mass spectrometry (e.g. MALDI-PSD). In a fourth step, (iv) the sequenced is determined applying the present invention. In a fifth step, (v) a database is queried using the newly identified "sequence tag" from step four and candidate proteins for PROTEIN 1 are identified by homology search (FIG. 4C). In a sixth step, (vi) the newly identified candidate PROTEIN 1 is subjected to a virtual digest (e.g. trypsin digest), the result of which is compared to the output of the original PMF analysis from step one. And finally, in a seventh step, (vii) such fragments are compiled which may be left over and do not fit with the virtual digest of candidate PROTEIN 1 (FIG. 4D). These potentially stem from PROTEIN 2 or e.g. a splice variant of PROTEIN 1 and can be identified with a second cycle of steps 1 through 7, and so forth.

The above described method enables quick identification of proteins but also identification of proteins within a protein mixture. Thus, e.g. 2D gels may be extracted and used for protein/peptide analysis. Previously the problem was that one single dot in such a 2D gel would actually comprise two or more proteins. Prior art sequencing technologies would often fail to give unambiguous results due to the multiple proteins/peptides present in the reaction.

An aspect of the disclosed invention is a computer program product. As should be clear, the disclosed teachings can be implemented in a computer that is enabled to perform instructions from a computer-readable media. The instructions include instructions for enabling the computer to perform the techniques for peptide sequencing from mass spectrograph data. The computer is not restricted to any type of computer, including but not limited to, a PC, a mini workstation and a mainframe computer. The techniques can also be applied remotely over the internet. In addition, the computer readable media include, but not limited to, CDs, floppies, ROMs, RAMs, hard disks as well as internet downloads.

The features disclosed in this specification, claims and/or the figures may be material for the realization of the invention in its various embodiments, taken in isolation or in various combinations thereof. Although the preferred embodiments have been disclosed for illustrative purposes, those skilled in the art will appreciate that various modifications and changes are possible, without departing from the scope and spirit of the invention as disclosed in the accompanying claims and such modifications and changes fall in the scope of the present invention defined in the claims.

What is claimed is:

1. A method of peptide sequencing from peptide fragment mass data, said method comprising:
   (a) obtaining peptide fragment mass data, said fragment mass data comprising a plurality of peak data;
   (b) deriving a plurality of candidate peptide sequences from said peptide fragment mass data;
   (c) calculating mass spectra for each candidate peptide sequence from said plurality of candidate peptide sequences; and
   (d) comparing said calculated mass spectra to said peptide fragment mass data for providing at least one identified peptide sequence;
   wherein the at least one identified peptide sequence is displayed in an output window;
   wherein said step (b) deriving said plurality of candidate peptide sequences comprises:
   calculating peptide fragment masses by adding to masses of a proton, hydronium ion, b1 ion and y1 ion masses of one amino acid or more amino acids;
   searching said plurality of peak data for masses matching said calculated peptide fragment masses to obtain resulting masses;
   annotating in all permutations said peak data with amino acid sequences that correspond to said calculated peptide fragment masses, thereby creating one or more potential sequences;
   extending said potential sequences from said matching masses by stepwise adding masses of one or more amino acids and searching for masses in said plurality of peak data that match said resulting masses;
   extending said stepwise additions until said resulting masses correspond to parental peptide masses or said parental peptide masses minus the mass of water, depending on whether the b or y ion series sequences are calculated;
   providing at least one identified peptide sequence by deleting sequences from said potential sequences that can not be extended to endpoints of said parental peptide masses, and
   deleting identical sequences generated in at least one of the foregoing steps from said potential sequences;
   wherein the foregoing steps are performed by a computer that is enabled to execute instructions to perform peptide sequencing from mass spectrograph data from a computer-readable media.

2. The method according to claim 1, wherein said potential sequence is scored according to the degree to which its theoretical fragment mass spectra match said plurality of peak data of step (a).

3. The method according to claim 1, further comprising a step of using said at least one identified peptide sequence as a query sequence for searching one or more peptide sequence databases in order to identify and retrieve one or more identical or similar sequences.

4. The method according to claim 3, wherein sequence differences between said query sequence and said one or more similar sequences retrieved form said one or more peptide sequence databases are annotated.

5. The method according to claim 1, wherein said peptide fragment mass data are generated by tandem mass spectrometric data including MALDI-TOF-PSD, MALDI-TOF/TOF, ESI-QTOF or ESI-Quad mass spectrometry.

6. A computer program product including computer-readable media said media comprising instructions to enable a computer to perform peptide sequencing from peptide fragment mass data, the instructions comprising:
   (a) obtaining peptide fragment mass data, wherein said fragment mass data comprises a plurality of peak data;
   (b) deriving a plurality of candidate peptide sequence from said peptide fragment mass data;
   (c) calculating mass spectra for each candidate peptide sequence from said plurality of candidate peptide sequence; and
   (d) comparing said calculated mass spectra to said peptide fragment mass data to provide at least one identified peptide sequence;

wherein the at least one identified peptide sequence is displayed in an output window;
wherein the computer-readable media is non-transitory; and
where the instruction for said step (b) deriving said plurality of candidate peptide sequences comprises:
calculating peptide fragment masses by adding to masses of a proton, hydronium ion, b1 ion and y1 ion masses of one amino acid or more amino acids;
searching said plurality of peak data for masses matching said calculated peptide fragment masses to obtain resulting masses;
annotating in all permutations said peak data with amino acid sequences that correspond to said calculated peptide fragment masses, thereby creating one or more potential sequences;
extending said potential sequences from matching masses by stepwise adding masses of one or more amino acids and searching for masses in said plurality of peak data that match said resulting masses;
extending said stepwise additions until said resulting masses correspond to parental peptide masses or said parental peptide masses minus the mass of water, depending on whether the b or y ion series sequences are calculated; and
providing at least one identified peptide sequence by deleting sequences from said potential sequences that can not be extended to endpoints of said parental peptide masses, and deleting identical sequences generated from at least one of the foregoing steps from said potential sequences.

7. The computer program product of claim 6, wherein said potential sequence is scored according to the degree to which its theoretical fragmentation mass spectra match said plurality of peak data of step (a).

8. The computer program product of claim 6, further comprising a step of using said at least one identified peptide sequence as a query sequence for searching one or more peptide sequence databases in order to identify and retrieve one or more identical or similar sequences.

9. The computer program product of claim 8, wherein sequence differences between said query sequence and said one or more similar sequences retrieved form said one or more peptide sequence databases are annotated.

10. The computer program product of claim 6, wherein said peptide fragment mass data are generated by tandem mass spectrometric data including MALDI-TOF-PSD, MALDI-TOF/TOF, ESI-QTOF or ESI-Quad mass spectrometry.

* * * * *